United States Patent
Gueret (12)

(10) Patent No.: US 6,280,765 B1
(45) Date of Patent: *Aug. 28, 2001

(54) PHARMACEUTICAL, COSMETIC OR DERMO-PHARMACEUTICAL PATCH FOR THE DELIVERY OF SEVERAL ACTIVE COMPOUNDS OF DIFFERENT NATURE

(75) Inventor: Jean-Louis H. Gueret, Paris (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/058,883

(22) Filed: Apr. 13, 1998

(30) Foreign Application Priority Data

Apr. 11, 1997 (FR) .................................................. 97 04498

(51) Int. Cl.$^7$ ................ A61K 9/70; A61K 9/00; A61L 15/00
(52) U.S. Cl. ................ 424/449; 424/400; 424/402; 424/443; 424/445; 424/447
(58) Field of Search .................................... 424/443, 400, 424/402, 445, 447, 449

(56) References Cited

U.S. PATENT DOCUMENTS

| 5,232,702 | * | 8/1993 | Pfister et al. | ............ | 424/448 |
| 5,707,648 | * | 1/1998 | Yiv | ............ | 424/450 |

FOREIGN PATENT DOCUMENTS

| 4210164 | 2/1993 | (DE) . |
| 314528 | 5/1989 | (EP) . |
| 764441 | 3/1997 | (EP) . |
| 2735024 | 12/1996 | (FR) . |

* cited by examiner

*Primary Examiner*—Shelley Dodson
(74) *Attorney, Agent, or Firm*—Oblon, Spivak, McClelland, Maier & Neustadt, P.C.

(57) ABSTRACT

Patch comprising a hydrophobic polymer layer bound to a support layer and containing: a) first particles of at least one water-soluble active compound, b) second particles of oil, c) at least one liposoluble active compound, d) third particles of a water-absorbing agent all of which are dispersed homogeneously in the polymer layer. This patch allows the packaging and controlled administration of an assembly of skin-nourishing and/or skin-repairing substances of different nature, and also has excellent adhesive power on the skin.

24 Claims, No Drawings

PHARMACEUTICAL, COSMETIC OR DERMO-PHARMACEUTICAL PATCH FOR THE DELIVERY OF SEVERAL ACTIVE COMPOUNDS OF DIFFERENT NATURE

BACKGROUND OF THE INVENTION

1. Field of the Invention

The present invention relates to a patch which allows the controlled release into the epidermis of at least two pharmaceutically, cosmetically or dermo-pharmaceutically active compounds, in particular compounds having different solubilities. According to the invention, this relates, in particular, to a first group of liposoluble active agents and to a second group of water-soluble active agents.

In the description of the present invention hereinbelow, the term "patch" denotes an active-agent delivery system having a composite structure in the form of layers which, when applied to the skin, ensures release of the active product by transdermal action.

As regards the liposoluble active compound, this is, in particular, a compound capable of being dissolved in an apolar medium such as an oily medium.

As regards the water-soluble active compound, it is in solid form, in particular in the form of a particulate powder or in the form of granules.

2. Description of the Prior Art

It is known to use patches which allow, by transdermal action, the penetration of active compounds.

Such patches generally have a structure containing several successive layers in the following order: a first layer, known as the support layer, which is generally occlusive, i.e. consisting of a material which is impermeable to the active compound, so as to prevent evaporation of the latter and promote the transdermal action; a second layer, known as the polymer layer, bound to the support layer and containing the active compound, it being possible for this layer to come into direct contact with the skin; optionally, in order to promote binding of the patch to the skin, a layer of an adhesive material applied to the surface of the polymer layer and permeable to the active compound; lastly, a detachable protective layer hermetically covering the polymer layer, so as to protect it against any external contamination during the storage time prior to the patch being used.

A patch structure consisting of an occlusive support layer and comprising, bound to the latter, a polymer layer made of a matrix of a silicone polymer including, in the dispersed state, fatty substances and hydrophilic active compounds, is known, in particular according to U.S. Pat. No. 5,232,702. This form of patch is more particularly suitable for delivering water-soluble active compounds and the patent does not describe the delivery of additional active compounds of lipophilic nature.

Moreover, document WO 96/14822 describes an occlusive patch of a form adapted for the treatment of wrinkles, of the abovementioned type containing a water-soluble active compound in powder form in an anhydrous matrix wherein the matrix may contain an oil, used as a penetration agent.

Furthermore, document FR-A-2,738,744 describes a patch for the controlled release of at least one cosmetically or dermo-pharmaceutically active compound, this patch containing a reservoir layer, bound to a support layer wherein the reservoir layer consists of a hydrophobic polymer matrix in which are dispersed particles of the active compound (which may be unstable in oxidizing medium) and particles of at least one water-absorbing agent, the reservoir layer being anhydrous.

A patch consisting of a silicone matrix containing a liposoluble active agent, a water-soluble active agent and an oil for increasing the penetration of the liposoluble active agent, this water-soluble active agent being in particulate form dispersed in the matrix, is also known from document DE-A-4,210,165.

SUMMARY OF THE INVENTION

The present invention relates to a controlled-delivery system containing an anhydrous polymer matrix in which is dispersed an oil in the form of droplets, this matrix being intended to release simultaneously lipophilic active compounds and hydrophilic active compounds. The use of an anhydrous polymer matrix in which an oil is dispersed has the advantage of being able to give a particularly flexible patch, designed to adhere to non-planar skin surfaces, with a high radius of curvature, and of not being hampered by regions of skin folds.

Tests have shown that in patches of the prior art, adhesion to the skin was difficult particularly when a relatively large proportion of oil was incorporated.

It has been found surprisingly, that the addition of a water-absorbing agent to the matrix leads to a substantial improvement in the adhesive power of the patch of the invention.

Moreover, the Inventor has observed that by dispersing in a hydrophobic polymer matrix, an appropriate amount of oil, in which a first lipophilic active compound is dissolved, a patch is obtained containing an anhydrous polymer layer but nevertheless allowing excellent controlled release of a second pulverulent active compound of hydrophilic nature.

The patch of the invention allows, in particular, the packaging and controlled administration of an assembly of skin-nourishing and/or skin-repairing substances of lipophilic and hydrophilic nature, and in particular lipophilic and hydrophilic active agents which have a tendency to inactivate each other when they are found in combination.

It has also been observed, entirely surprisingly and unexpectedly, that it is possible to package one (or more) hydrophilic active compound(s), one (or more) lipophilic active compound(s) and one (or more) oil(s) in the same polymer matrix. Thus, it is possible to prepare, for example, a stable combination of particles of a water-soluble compound, which is unstable in aqueous medium or in the open air and/or of a liposoluble active compound, which is also unstable in aqueous medium or in the open air, with an unsaturated oil, which has a drying effect in the open air, without any risk of degradation of the active compounds and without any risk of hardening of the oil.

DETAILED DESCRIPTION OF THE INVENTION

The subject of the present invention is a pharmaceutical, cosmetic or dermo-pharmaceutical patch containing a hydrophobic polymer layer bound to a support layer and containing: a) first particles of at least one water-soluble active compound, b) second particles of oil, c) at least one liposoluble active compound, and d) third particles of a water-absorbing agent, dispersed homogeneously in the polymer layer.

According to a first embodiment, the liposoluble active compound is dissolved in the oil.

According to another embodiment, the liposoluble active compound is in particulate form, in the form of powder or granules, dispersed in the polymer layer.

The oil which can be used in accordance with the invention can be chosen from the following oils, alone or as a mixture, among which mention may be made of: oils of animal, plant or mineral origin, and in particular animal or plant oils formed by fatty acid esters of polyols, in particular liquid triglycerides, for example sunflower oil, corn oil, soybean oil, marrow oil, grapeseed oil, sesame oil, hazelnut oil, pistachio oil, apricot oil, almond oil or avocado oil; fish oils, glyceryl tricaprocaprylate, or plant or animal oils of formula $R_1COOR_2$ in which $R_1$ represents a higher fatty acid residue containing from 7 to 19 carbon atoms and $R_2$ represents a branched hydrocarbon chain containing from 3 to 20 carbon atoms, for example purcellin oil, wheatgerm oil, beauty-leaf oil, sesame oil, coriander oil, safflower oil, passion flower oil, musk rose oil, macadamia oil, fruit (grape, blackcurrant, orange, kiwi) seed oil, rapeseed oil, coconut oil, groundnut oil, evening primrose oil, palm oil, castor oil, flax oil, jojoba oil, chia oil, olive oil or cereal germ oil such as wheatgerm oil, rice bran oil, karite butter; acetyl glycerides; alkyl or polyalkyl octanoates, decanoates or ricinoleates; fatty acid triglycerides; glycerides; liquid paraffin, liquid petroleum jelly, perhydrosqualene; fatty alcohols (stearyl alcohol, cetyl alcohol) and fatty acids (stearic acid) and esters thereof; poly($C_1$–$C_{20}$) alkyl siloxanes and in particular those containing trimethyl silyl end groups, preferably those whose viscosity is less than 0.06 $m^2$/s, among which mention may be made of linear polydimethylsiloxanes and alkylmethylpolysiloxanes such as cetyldimethicone (CTFA name).

Suitable oils also include partially fluorinated hydrocarbon oils or perfluoro oils, and in particular perfluoropolyethers and perfluoroalkanes.

The oily phase, i.e. the droplets of oil dispersed in the polymer layer, is present in a proportion ranging from about 0.1% to about 30% by weight relative to the total weight of the composition. Preferably, this percentage is between about 5% and about 25% and most preferably between about 10% and 20%.

When the products according to the invention are used for cosmetic treatment of the skin or for dermatological purposes, the active compound contained in the oily phase is more particularly chosen from antioxidants, anti-free-radical agents, moisturizers, depigmenting agents, liporegulators, slimming agents, antiacne agents, antipsoriasis agents, antiseborrhoeic agents, antihistamines, anti-ageing agents, anti-wrinkle agents, keratolytic agents, anti-inflammatory agents, refreshing agents, cicatrizing agents, vascular protectors, antibacterial agents, antifungal agents, antiperspirants, skin conditioners, immunoregulators nourishing agents and the like.

Among the lipophilic active agents dissolved in the oily phase, which can be used in the context of the present invention, mention may be made, for example, of the following compounds:

D-α-tocopherol, DL-α-tocopherol, D-α-tocopheryl acetate, DL-α-tocopheryl acetate, ascorbyl palmitate, vitamin F and vitamin F glycerides, vitamin D, vitamin $D_2$, vitamin $D_3$, retinol, retinol esters, retinyl palmitate, retinyl propionate, β-carotene, D-panthenol, famesol, farnesyl acetate; jojoba oils and blackcurrant oils rich in essential fatty acids; 5-n-octanoylsalicylic acid and esters thereof, salicylic acid and esters thereof; alkyl esters of α-hydroxy acids such as citric acid, lactic acid, glycolic acid; asiatic acid, madecassic acid, asiaticoside, total extract of Centella asiatica, β-glycyrrhetinic acid, α-bisabolol, ceramides such as 2-oleoylamino- 1,3-octadecane; phytanetriol, phospholipids of marine origin which are rich in polyunsaturated essential fatty acids, ethoxyquine; extract of rosemary, extract of balm, quercetin, extract of dried microalgae, anti-inflammatory agents, such as steroidal anti-inflammatory agents, and biostimulants, for example hormones or compounds for the synthesis of lipids and/or proteins.

The concentration of the lipophilic active compound in the oily phase which can be used depends on the nature of the plant oil used. Typically, this concentration can range from about 0.01% to 20% by weight relative to the total weight of the oily phase. Preferably, this percentage is in the range of about 1% to about 10%.

Where appropriate, the oily phase can also contain lipophilic surfactants, for example sucrose distearate, diglyceryldistearate, tetraglyceryl tristearate, decaglyceryl decastearate, diglyceryl monostearate, hexaglyceyl tristearate, decaglyceryl pentastearate, sorbitan monostearate, sorbitan tristearate, diethylene glycol monostearate, the ester of glycerol and of palmitic acid and stearic acid, monostearate polyoxyethylenated with 2 OE (containing 2 oxyethylene units), glyceryl mono- and dibehenate and pentaerythrityl tetrastearate.

When the compositions in accordance with the invention are used for the cosmetic treatment of the skin or for dermatological purposes, the particles of water-soluble solid active compound(s) is (are) chosen from conventional hydrophilic active agents such as antioxidants, anti-free-radical agents, moisturizers, depigmenting agents, liporegulators, slimming agents, antiacne agents, antiseborrhoeic agents, anti-ageing agents, anti-wrinkle agents, keratolytic agents, anti-inflammatory agents, refreshing agents, cicatrizing agents, vascular protectors, antibacterial agents, antifungal agents, antiperspirants, deodorants, skin conditioners, immnunoregulators and nourishing agents.

In the patches according to the present invention, the hydrophilic active compound can be chosen, for example, from ascorbic acid and biologically compatible salts thereof, enzymes, antibiotics such as clindamycin phosphate, components with a surfactant effect such as protein powders from soybean or from wheat, α-hydroxy acids and salts thereof, hydroxylated polyacids, sucroses and derivatives thereof, urea, amino acids, oligopeptides, water-soluble plant extracts and yeasts, hydrolysates of proteins such as collagen and elastin, hyaluronic acid, mucopolysaccharides, vitamins $B_2$, $B_6$, H and PP, panthenol, folic acid, acetyl salicyclic acid, allantoin, glycyrrhetinic acid, kojic acid, caffeine hydroquinone, etc.

Advantageously, the water-soluble active is compound is present in the polymer layer in a proportion ranging from about 0.2% to about 20% by weight relative to the total weight of the said layer. Preferably, the percentage ranges from about 2% to about 10%.

Preferably, the particles of the water-soluble active compound have an average size of between about 0.2 μm and about 0.5 mm.

According to an advantageous aspect of the invention, one can package one (or more) hydrolysis-sensitive, hydrophilic active compound(s), one (or more) oxidation-sensitive lipophilic active compound(s) and one (or more) oil(s), which is (are) also oxidation-sensitive, in the same matrix. Under these conditions, a water-soluble active agent can be used which is incompatible with the liposoluble active compound or with the oil, in standard topical preparations of the cream type or lotion type. Thus, it is possible, for example, to prepare a combination of particles of vitamin C with an unsaturated oil containing vitamin A without any risk of the vitamins degrading and without any risk of polymerization of the oil.

Advantageously, the matrix forming the polymer layer can contain particles of at least one water-absorbing agent which are dispersed homogeneously in the said matrix. On contact with skin moisture, the particles of the water-absorbing agent take up water, thus promoting the solubilization of the water-soluble, solid active compound. In this way, by means of the "in situ" solubilization of the water-soluble active agent, its bioavailability is virtually instantaneous and any possible interaction with the other compounds present in the polymer layer is minimized. The skin moisture can also act as the solubilizing agent for the water-soluble active agent since the support layer of the patch creates occlusive conditions.

Among the water-absorbing agents which can be present in the hydrophobic polymer matrix in the dispersed state, mention may be made preferably of superabsorbent crosslinked polyacrylates with a high degree of swelling in water, such as those sold by the company Norsolor under the name Aquakeep®; polyvinyl alcohol; carboxyvinyl polymers such as those sold by the company Goodrich under the names "Carbopol"®; semisynthetic cellulose derivatives such as carboxymethylcellulose; natural substances such as starches, natural gums (guar gum, gum arabic, gum tragacanth), casein, phytocolloids (carrageenates, alginates, agar-agar), cotton fibres, and gelatin.

It is also possible to use a water-absorbing agent in the form of particles of a powder of freeze-dried or sprayed emulsion. Advantageously, the particles of the water-absorbing agent have an average size of between about 0.2 μm and about 1.5 mm.

A particularly preferred embodiment of the invention is to use "superabsorbent" crosslinked polyacrylates whose presence in the dispersed state in the hydrophobic polymer matrix promotes, after hydration, better diffusion of the hydrophilic active compound. By virtue of the presence of these "superabsorbent" agents, better adhesion of the patch to the skin is also obtained, especially when prolonged application is desired, The water-absorbing agent as defined above is preferably present in a proportion ranging from about 0.1% to about 30% by weight, and more particularly ranging from about 0.5% to about 10% relative to the total weight of the polymer layer.

In the patches according to the present invention, the hydrophobic polymer matrix, for example, may be based on a silicone polymer or a polyurethane such as of the polyester polyurethane or polyether polyurethane type.

When the polymer matrix is based on a silicone polymer, the polymer is preferably chosen from linear organopolysiloxanes substituted on the silicon atom with groups chosen from a $C_1$–$C_6$ alkyl, aryl or ar ($C_1$–$C_2$ alkyl) group, the end silicon atoms being trisubstituted. Such organopolysiloxanes are described in particular in U.S. Pat. No. 2,541,137, 2,723,966, 2,863,846, 2,890,188, 2,927,907, 3,002,951 and 3,035,016.

A silicone prepolymer containing the following units is particularly preferred:

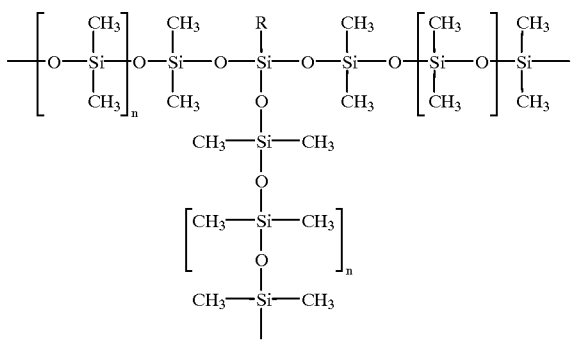

in which:
R represents an alkyl or alkoxy group containing from about 1 to 7 carbon atoms, an ethylenically unsaturated group such as vinyl or an aryl group such as phenyl, and n is chosen in the range from about 100 to about 5000.

Suitable organopolysiloxanes which can be used according to the invention are those known under the names Silastic 382®, Q7-4635®, Q7-4650®, Q7-4735®, Q7-4750®, 4765®, MDX 4-4210® and DC 3.6486® sold by the company Dow Corning.

The silicone polymer is preferably crosslinkable at moderate temperatures such as room temperature, using a crosslinking catalyst which is biologically acceptable in the resulting polymer matrix and which is compatible with the active compound dispersed in this matrix.

The term crosslinking catalyst is understood to refer to the combination of a crosslinking agent and a catalyst.

When the silicone polymer contains hydroxyl groups, such as end hydroxyl groups, tetrapropoxysilane [Si—(O—$CH_2$—$CH_2$—$CH_3$)$_4$] in combination with a tin-based catalyst may be a suitable crosslinking agent.

When the silicone polymer contains vinyl groups, it can be crosslinked in the presence of a dimethyl silicone polymer in combination with a catalyst such as a platinum-based catalyst.

When the polymer matrix is based on a polyurethane, it can be a prepolymer of the polyester-polyol or polyether-polyol type known in the art. Among the polyester-polyols, mention may be made of those obtained by reaction of di- or trifunctional alcohols with acids such as adipic acid, terephthalic acid and, more generally, any other multifunctional acid. Among the polyether-polyols, mention may be made of those obtained by reacting diols such as ethylene glycol or propylene glycol or polyols such as trimethylolpropane, glycerol, pentaerythritol, sorbitol etc. with oxides such as ethylene oxide, propylene oxide or a mixture thereof.

The polyaddition agent for formation of the polyurethanes is an isocyanate or polyisocyanate, in particular toluene diisocyanate, diphenylmethane 4,4'-diisocyanate, naphthalene 1,5-diisocyanate or isophorone diisocyanate.

The crosslinking catalyst or the polyaddition agent is preferably used in an amount such that the crosslinking or the polyaddition is not complete. This provides the polymer layer with an intrinsic self-adhesive nature such that it is unnecessary to coat the support layer with an adhesive layer.

Lastly, in order to strengthen the resistance to elongation of the polymer matrix, the polymer layer can contain a frame, for example, of a perforated sheet of a plastic material, a sheet of a perforated nonwoven material or a non-stretchable gauze, the nonwoven material or the gauze consisting of natural or synthetic fibres, such as polyamide, as described in French patent No. 92/05623 (FR-A-2,620, 914).

The support layer or occlusive layer for the patches according to the present invention can consist of any suitable material which is impermeable to the active compounds contained in the adjacent polymer layer.

The support layer not only serves to support the polymer layer but also serves as a protective coating for it.

The support layer can be of the same size as the polymer layer or larger in size, such that it extends outwards beyond the periphery of the polymer layer, wherein the surface which surrounds the polymer layer can optionally receive adhesive means.

Among the materials suitable for the support layer, mention may be made of high- and low-density polyethylene films, polypropylene films, polyvinyl chloride films, films made of polyester such as polyethylene phthalate, films made of ethylene/vinyl acetate copolymers and polyurethane films. These materials can also be present in laminated form with at least one sheet of metal such as a sheet of aluminum. The support layer can be of any suitable thickness which will provide the desired support and protection functions. Preferably, the thickness of the support layer is between about 0.2 mm and about 1.5 mm.

The patches according to the present invention can also be protected by a detachable or peelable protective layer adjacent to the polymer layer and/or by packaging in a suitable package, particularly one which is impermeable to water and to steam.

When the polymer layer is protected by a detachable protective layer, this protective layer is removed at the time of use. It can consist of any material which is impermeable to the active compound as well as any other component present in the polymer matrix. Among the materials which can be used, mention may be made of a sheet of silicone paper or a sheet of thermoplastic material treated to make it anti-adhesive, for example using a varnish. Preferably, this detachable protective layer consists of polyethylene.

The patches according to the present invention can be cut according to an appropriate contour corresponding to the region of skin surface to be treated, for example in the form of a mask for application to the face, especially for application around the eyes, on the bags under the eyes or on the forehead. Needless to say, the patches according to the present invention can be cut into any other shape required for application to a defined region of the body. In general, the size of a patch in accordance with the invention is between about 0.25 cm$^2$ to about 500 cm$^2$. Thus, a patch intended for the depigmentation of pigmented skin blemishes can be small in size, less than 1 Cm$^2$, whereas a patch with a slimming action can have a large surface area, which is sufficient to cover part of a thigh, for example.

The patches thus made and cut up can be used, after removal of the detachable protective layer, on a surface of skin to be treated, by applying them directly to the skin, the moisture of this skin making it possible to obtain the desired release of the hydrophilic active compounds- They can also be presoaked in water for a period preferably for between about 5 and 30 seconds, or they can be applied to the skin after having been premoistened, for example using a sponge.

In general, the perspiration moisture of the skin is sufficient to obtain the release of the hydrophilic active compound onto the surface of the skin to be treated, from the hydrophobic polymer matrix containing it.

In the patches according to one embodiment of the present invention, the polymer matrix constituting the polymer layer is prepared by intimate mixing with stirring the polymer (e.g., polyurethane or silicone prepolymer), the hydrophilic active compounds and the water-absorbing agent, which are both in the form of particles, as well as the oil containing the dissolved lipophilic compounds mentioned above.

Either a crosslinking catalyst, if the prepolymer is a silicone polymer, or an isocyanate or polyisocyanate, if the prepolymer is a polyester-polyol or a polyether-polyol, is then added, at a low temperature (generally room temperature) to the mixture thus obtained.

The mixture is then introduced into a hopper and poured onto a sheet of, for example, polyethylene, which constitutes the detachable or peelable protective film for the patch. A scraper is positioned downstream of the hopper, this scraper allowing the thickness of the polymer layer of the polymer matrix to be evened out, this thickness generally being between about 0.1 mm and 12 mm.

A frame sheet as defined above may be subsequently applied, followed before calendering, by a sheet of the support or occlusive layer which can also be a sheet of polyethylene.

The polymerization or polyaddition is preferably carried out at room temperature, this being in order not to deteriorate the active compounds. In general, the polymerization or polyaddition is complete after about 24 hours at room temperature.

After calendering and before the polymerization or polyaddition is complete, the composite structure obtained can be cut up immediately into the desired shapes, thereby allowing crimped edges to be obtained which avoids any running.

EXAMPLES

The Examples which follow illustrate the present invention but are not intended to be limiting unless otherwise specified.

Example 1

10 g of sweet almond oil containing 0.2 g of all trans-retinol and 2 g of microcrystalline vitamin C are added to 8 g of polyacrylate powder (Aquakeep® sold by the company Norsolor). Subsequently, 43 g of DC3.6486® organopolysiloxane (sold by the company Dow Corning) and 1.7 g of Medical Grade Curing Agent crosslinking catalyst are added with stirring at 1500 revolutions/min for a few minutes.

The product thus homogenized is introduced into a hopper and is spread out using a scraper into a layer 0.8 mm thick on a sheet of polyethylene 200 μm thick. This sheet can be surface-pretreated in order to reduce its adhesion. A frame consisting of a polyethylene or polyamide gauze containing mesh with an aperture of 1 mm and a thiclness of 0.3 mm is applied to the sheet of polyethylene thus coated.

A polyethylene film (without anti-adhesive treatment) 30 μm in thickness, which constitutes the support or occlusive layer of the patch, is then applied and calendering is carried out on the assembly. An assembly containing an occlusive support layer and a self-adhesive polymer layer formed of a partially crosslinlked silicone polymer matrix is thus obtained, this assembly also comprising a detachable protective layer.

Different patch shapes which depend on the desired uses can be made by being cut out of this assembly.

After cutting-out, the patches arc then packaged in polyethylene sachets. During use, after removal of the detachable protective layer, the patch is applied directly around an eye, for example for a period of about 30 minutes. After the patch has been removed, it is observed visually that the area around the eye treated with this patch has a substantially smoother and more refreshed appearance than that of the other untreated eye. This patch has good adhesive power on the skin.

Example 2

12 g of castor oil containing 0.3 g of D-α-tocopherol and 2 g of microcrystalline sodium lactate are added to 8 g of polyacrylate powder (Aquakeep® sold by the company Norsolor). Subsequently, 43 g of DC3.6486® organopolysiloxane (sold by the company Dow Corning) and 1.7 g of Medical Grade Curing Agent crosslinking catalyst are added, with stirring at 1500 revolutions/min, and continued for a few minutes.

A patch is made in a similar manner to that of Example 1. After applying this patch to the skin for 12 hours, good adhesive power is again observed.

A test of conservation at 45° C. for 48 hours demonstrates that neither the castor oil nor the tocopherol is degraded.

Example 3

10 g of jojoba oil, 0.6 g of β-carotene and 1.5 g of microcrystalline hydroxyproline are added to 8 g of polyacrylate powder (Aquakeep® sold by the company Norsolor). Thereafter, 43 g of DC3.6486® organopolysiloxane (sold by the company Dow Corning) and 1.7 g of Medical Grade Curing Agent crosslinking catalyst are added, with stirring at 1500 revolutions/min, for a few minutes.

A patch is made in a similar manner to that of Example 1, this patch having repairing action on light-damaged skin, and emollient and cicatrizing action. The adhesive power of this patch on the skin, evaluated after 12 hours, proved to be satisfactory.

Example 4

1.5 g of urea and 0.5 g of caffeine powder are added to 10 g of sesame oil containing 0.2 g of hexyl nicotinate. Subsequently, 43 g of DC3.6486® organopolysiloxane (sold by the company Dow Corning) and 1.7 g of Medical Grade Curing Agent crosslinking catalyst are added with stirring at 1500 revolutions/min, and continued for a few minutes.

A patch is made in a similar manner to that of Example 1. After applying this patch for 15 minutes, it increases the vascular microcirculation of the skin and promotes the metabolism of subcutaneous fats.

The present application is based on French Patent Application No. 9704498, filed Apr. 11, 1997, the disclosure thereof being incorporated herein by reference in its entirety.

What is claimed is:

1. A patch comprising a hydrophobic polymer layer attached to a support layer, the polymer layer containing:
   a) first solid particles of at least one water-soluble active compound,
   b) second particles of at least one oil,
   c) at least one liposoluble active compound, and
   d) third solid particles of a water-absorbing agent, all dispersed homogeneously in the polymer layer.

2. A patch according to claim 1, wherein the liposoluble active compound is dissolved in the oil.

3. A patch according to claim 1, wherein the liposoluble active compound is in particulate form dispersed in the polymer layer.

4. A patch according to claim 1, wherein the water-absorbing agent is selected from superabsorbent crosslinked polyacrylates, polyvinyl alcohol, carboxyvinyl polymers, semisynthetic cellulose derivatives, starches, guar gum, gum arabic, gum tragacanth, casein, phytocolloids, cotton fibres, or gelatin.

5. A patch according to claim 1, wherein the water-absorbing agent is in the form of powder particles prepared by freeze-drying or sprayed emulsion.

6. A patch according to claim 1, wherein the water-absorbing agent is present in the polymer layer in a proportion ranging from about 0.1% to about 30% by weight relative to the total weight of the said layer.

7. A patch according to claim 1, wherein the particles of the water-absorbing agent have an average size of between about 0.2 μm and about 1.5 mm.

8. A patch according to claim 1, wherein the oil is selected from mineral, animal, plant or synthetic oils or mixtures thereof.

9. A patch according to claim 1, wherein the oil is present in the polymer layer in a proportion ranging from about 0.1% to about 30% relative to the total weight of the polymer layer.

10. A patch according to claim 1, wherein the liposoluble active compound is present in the polymer layer in a proportion ranging from about 0.01% to about 20% by weight relative to the total weight of the oil.

11. A patch according to claim 1, wherein the liposoluble active compound is selected from D-α-tocopherol, DL-α-tocopherol, D-α-tocopheryl acetate, DL-α-tocopheryl acetate, ascorbyl palmitate, vitamin F and vitamin F glycerides, vitamin D, vitamin $D_2$, vitamin $D_3$, retinol, retinol esters, retinyl palmitate, retinyl propionate, β-carotene, D-panthenol, farnesol, farnesyl acetate; jojoba oils and blackcurrant oils rich in essential fatty acids; salicylic acid and esters thereof, 5-n-octanoylsalicylic acid and esters thereof, alkyl esters of α-hydroxy acids, asiatic acid, madecassic acid, asiaticoside, total extract of Centella asiatica, β-glycyrrhetinic acid, α-bisabolol, ceramides, phytanetriol, phospholipids of marine origin which are rich in polyunsaturated essential fatty acids, ethoxyquine; extract of rosemary, extract of balm, quercetin, extract of dried microalgae or steroidal anti-inflammatory agents.

12. A patch according to claim 1, wherein the water-soluble active compound is present in the polymer layer in a proportion ranging from about 0.2% to about 20% by weight relative to the total weight of the said layer.

13. A patch according to claim 1, wherein the water-soluble active compound is in a particulate form in which the average particle size is between about 0.2 μm and about 0.5 mm.

14. A patch according to claim 1, wherein the water-soluble active compound is selected from ascorbic acid and biologically compatible salts thereof, enzymes, antibiotics, components with a surfactant effect, α-hydroxy acids and salts thereof, hydroxylated polyacids, sucroses and derivatives thereof, urea, amino acids, oligopeptides, water-soluble plant extracts and yeasts, protein hydrolysates, hyaluronic acid, mucopolysaccharides, vitamins $B_2$, $B_6$, H and PP, panthenol, folic acid, acetylsalicyclic acid, allantoin, glycyrrhetinic acid, kojic acid, caffeine or hydroquinone.

15. A patch according to claim 1, wherein the hydrophobic polymer layer is a silicone or a polyurethane.

16. A patch according to claim 15 wherein the silicone is obtained by crosslinking a linear organopolysiloxane substituted on the silicon atom with groups chosen from a $C_1$–$C_6$ alkyl, aryl or ar ($C_1$–$C_2$ alkyl) group, the end silicon atoms being trisubstituted with a $C_1$–$C_6$ alkyl group.

17. A patch according to claim 16, wherein the silicone contains the following units:

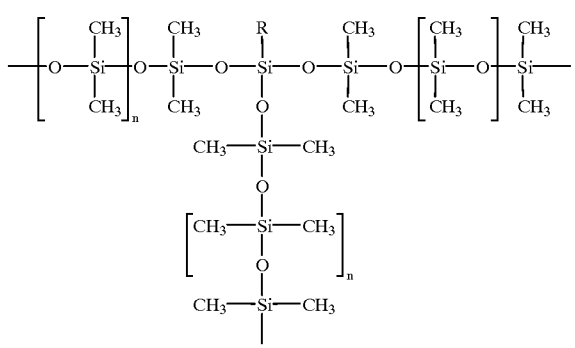

in which:

R represents an alkyl or alkoxy group containing from 1 to 7 carbon atoms, an ethylenically unsaturated group or an aryl group, and in which n is in the range from about 100 to about 5000.

18. A patch according to claim 15, wherein the polyurethane is obtained by polyaddition of a polyester-polyol or a polyether-polyol in the presence of an isocyanate or polyisocyanate.

19. A patch according to claim 1, wherein a frame is inserted between the polymer layer and the support layer.

20. A patch according to claim 19, wherein the frame is a perforated sheet of a plastic material or a sheet of a nonwoven material of natural or synthetic fibres or a non-stretchable gauze made of natural or synthetic fibres.

21. A patch according to claim 1, wherein the thickness of the polymer layer is between about 0.1 mm and 12 mm.

22. A patch according to claim 1, wherein the support layer comprises a polymer chosen from high- and low-density polyethylenes, polypropylenes, polyvinyl chlorides, copolymers of ethylene and vinyl acetate, polyesters or polyurethanes.

23. A patch according to claim 1, wherein the thickness of the support layer is between about 0.2 mm and 1.5 mm.

24. A patch according to claim 1, which is self-adhesive.

* * * * *